United States Patent
Zhou

(10) Patent No.: US 12,419,787 B2
(45) Date of Patent: Sep. 23, 2025

(54) SLEEP NOISE-PROOF STRUCTURE

(71) Applicant: Guoqing Zhou, Dongguan (CN)

(72) Inventor: Guoqing Zhou, Dongguan (CN)

(73) Assignee: Dongguan Pengteng Hardware and Electronics Co., Ltd, Dongguan (CN)

( * ) Notice: Subject to any disclaimer, the term of this patent is extended or adjusted under 35 U.S.C. 154(b) by 66 days.

(21) Appl. No.: 18/622,888

(22) Filed: Mar. 30, 2024

(65) Prior Publication Data

US 2024/0350318 A1 Oct. 24, 2024

(30) Foreign Application Priority Data

Apr. 19, 2023 (CN) .......................... 202320898817.X

(51) Int. Cl.
*A61F 11/12* (2006.01)
*A61F 9/04* (2006.01)

(52) U.S. Cl.
CPC ................. *A61F 11/12* (2013.01); *A61F 9/04* (2013.01)

(58) Field of Classification Search
CPC ......... A42B 3/04; A42B 3/0406; A42B 3/042; A42B 3/16–166; A42B 3/18; A42B 3/185; H04R 1/10–46; A61F 11/06–145; A61F 9/02–068

See application file for complete search history.

(56) References Cited

U.S. PATENT DOCUMENTS

| | | | | |
|---|---|---|---|---|
| 4,683,587 A | * | 7/1987 | Silverman | H04R 1/44 381/189 |
| 5,581,821 A | * | 12/1996 | Nakano | A61F 11/12 181/135 |
| 6,067,664 A | * | 5/2000 | Cortes | A61F 9/029 2/209 |
| 7,810,750 B2 | * | 10/2010 | Abreu | G02C 5/143 351/159.75 |
| 2003/0079935 A1 | * | 5/2003 | Weise | A61F 11/12 181/129 |
| 2018/0250168 A1 | * | 9/2018 | Herring | H04R 1/1016 |

FOREIGN PATENT DOCUMENTS

KR 20190002755 U * 11/2019 .............. A61F 11/08

* cited by examiner

*Primary Examiner* — Michelle J Lee

(57) ABSTRACT

The present invention falls within the field of articles for daily use, and particularly relates to a sleep noise-proof structure provided on an eye-shrouding member being an eye patch or a sleeping cap and having an eye shield for shrouding the eyes, wherein the sleep noise-proof structure comprises two wires and two earplugs, the wires have a first end and a second end, and the first end is fixedly connected to the front side of the eye shield, and the second end is connected to an earplug. Since the earplug is connected to the front side of the eye shield with a wire, not only the problem of loss of the earplug can be prevented, but also the ear cannot be tightened and the overall comfort can be increased for a better experience.

6 Claims, 8 Drawing Sheets

SLEEP NOISE-PROOF STRUCTURE

TECHNICAL FIELD

The present invention falls within the field of articles for daily use, and particularly relates to a sleep noise-proof structure.

BACKGROUND ART

Nowadays, people cannot take a good rest because they are more and more busy with their work and study, so there are eye patches, earplugs and other products for assisting sleep, using the eye patches to shield the eyes can either alleviate the fatigue of the eyes or block sunlight, and the earplugs can isolate noise and avoid disturbance. However, in one aspect, the conventional eye patches and the earplugs are formed in a separate structure, which means that the earplugs can be easily dropped when the user is asleep due to unconscious friction without connecting members, and the earplugs are small objects which are inconvenient to use and store. There is also an eye patch or a sleep eye patch having an earphone function, which can eliminate external noise by using an earphone. For example, Chinese patent No. CN 217723888U discloses an eye patch. The patent specifically discloses that the device comprises an eye patch body for wearing on the head and shielding the eye region, wherein both sides of the eye patch body are detachably equipped with a bone conduction earphone mounted and fixed in a snap-fit manner, and a mounting hole is provided on the eye patch body to cooperate with the bone conduction earphone.

In the eye patch disclosed in the above-mentioned patent document, a user wears a body on the face of a human body while using the eye patch, and bandage parts on both sides of the body are wound around a part of the back brain of the human body and fixed by a touch fastener. In order to achieve that the external noise interferes with the rest of the user, the body bandage part is used to wrap an ear band of the human body, and the user can also be provided with music through the earphone, etc., but wearing the bandage part of the eye patch body for a long time may snare the user's ear for a long time, causing a problem of discomfort to the user's ear and affecting the user's sleep.

SUMMARY OF THE INVENTION

An objective of the present invention is to provide a sleep noise-proof structure, which aims to solve the above problems.

In order to achieve the above-mentioned objective, the present invention provides a sleep noise-proof structure provided on an eye-shrouding member being an eye patch or a sleeping cap and having an eye shield for shielding an eye, the sleep noise-proof structure comprising two wires and two earplugs, the wires having a first end and a second end, the first end being fixedly connected to a front side of the eye shield, the second end being connected to the earplugs, wherein the wires are stretching wires, the second end of the wire is freely stretchable, the sleep noise-proof structure further comprises a reel device comprising a mounting housing, a wire spool, a winding spring and a positioning piece; the mounting housing is arranged on the front side of the eye shield, a mounting cavity is arranged in the mounting housing, a support shaft is arranged in the mounting cavity, and the wire spool is rotatably sleeved on the support shaft; a concave cavity is provided on the bottom side of the wire spool, the winding spring is provided to be wound in the concave cavity, and one end of the winding spring is snap-fit with the support shaft, and the other end thereof is snap-fit with the wire spool; the first end of the wire is wound around the wire spool and a second end extends out of the mounting cavity; and the positioning member is provided within the mounting cavity for positioning the wire spool.

Further, two wire grooves are provided on the wire spool, and one wire is connected to each wire groove.

Further, the number of reel devices is two and each of the wires is connected to one of the reel devices.

Further, the positioning member includes a track board and a retaining ring. The track board is provided on one side of the wire spool, a limiting cavity is provided on an upper end face of the track board, and an outer guide, a limiting member and an inner guide are provided in the limiting cavity. One end of the limiting member is provided with a limiting slot, an outlet is formed between one end of the outer guide and one end of the limiting slot of the limiting member, and the other end of the outer guide and one end of the limiting member facing away from the limiting slot form an inlet; the outer side of the outer guide and the inner side of the limiting cavity form an outer track, the inner side of the limiting member and the outer side of the inner guide form an inner track, the inner guide has a high point away from the center of the support shaft, the high point is arranged close to the outlet, the inner side of the limiting cavity is provided with a guide boss extending towards the inlet, the guide boss, and the inlet, the outlet and the high point are successively distributed around the center of the support shaft. A guide sliding groove is provided in the mounting housing, a retaining ring is slidably provided in the guide sliding groove, and the retaining ring is provided with a limiting column extending into the limiting cavity.

Further, the sleep noise-proof structure further comprises a casing, a Bluetooth earphone control module and a battery, wherein the casing is arranged on the front side of the eye shield. The Bluetooth earphone control module, the battery and the reel device are all provided in the casing. The wire is an earphone wire and is electrically connected to a control module of the Bluetooth earphone, and a loudspeaker module is provided in the earplug.

Further, the sleep noise-proof structure further comprises a clip board, a clip groove is provided on the back side of the mounting housing, the clip board is provided with a snap, and the snap passes through the eye shield and is engaged with the clip groove.

The above-mentioned technical solution or solutions of a sleep noise-proof structure provided by embodiments of the present invention have at least the following technical effects: when the user is at rest, after wearing the eye-shrouding member of the present embodiment, the eye-shrouding member is placed in front of the eyes to shield light and obtain sufficient eye rest. In addition, the earplug may be pulled from the front side of the eye and the wire pulled back from the front side of the eye shield to insert the earplug into the ear. In this way, a person can be prevented from being disturbed by external noise during rest. Since the earplug is connected to the front side of the eye shield with a wire, not only the problem of loss of the earplug can be prevented, but also the ear cannot be tightened and the overall comfort can be increased for a better experience.

BRIEF DESCRIPTION OF THE DRAWINGS

In order to explain the technical solutions in the embodiments of the present invention more clearly, the following will briefly introduce the embodiments or the drawings required to be used in the description of the prior art; obviously, the drawings in the description below are merely some embodiments of the present invention, and it would have been obvious for a person skilled in the art to obtain other drawings according to these drawings without involving any inventive effort.

REFERENCE NUMERALS

100. eye-shrouding member; 110. wire; 120. earplug; 130. eye shield;
200. reel device; 201. mounting cavity; 202. support shaft; 210. wire spool; 211. concave cavity;
212. wire groove; 220. winding spring; 240. mounting housing;
300. positioning member; 310. track board; 350. retaining ring; 311. limiting cavity; 312. outer guide; 313. limiting member; 314. inner guide; 315. limiting slot; 316. outlet; 317. inlet; 318. outer track; 319. inner track; 320. high point; 321. guide boss; 322. guide sliding groove; 323. limiting column;
500. clip board; 510. clip groove; 520. snap;
600. Bluetooth earphone control module; 601. casing; 602. battery.

DETAILED DESCRIPTION OF THE INVENTION

Figure 1:
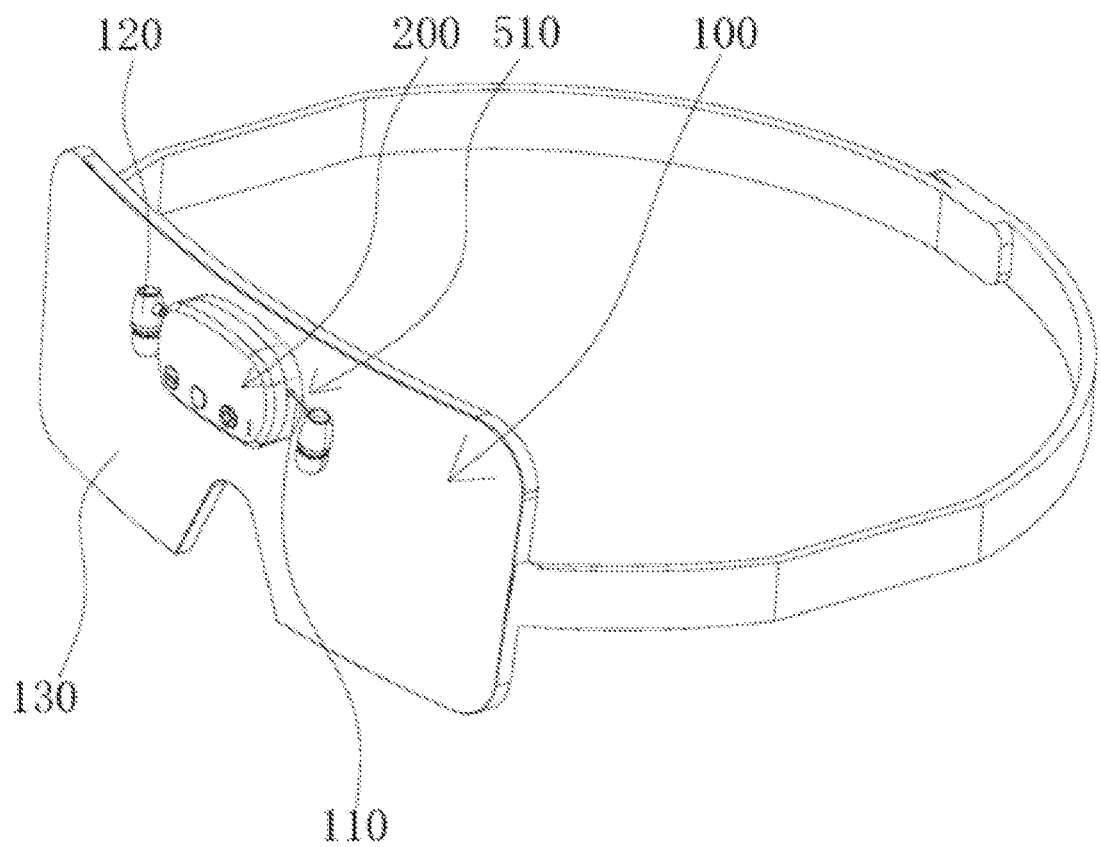
FIG. 1 is a front view of a sleep noise-proof structure according to an embodiment of the present invention.
Figure 2:
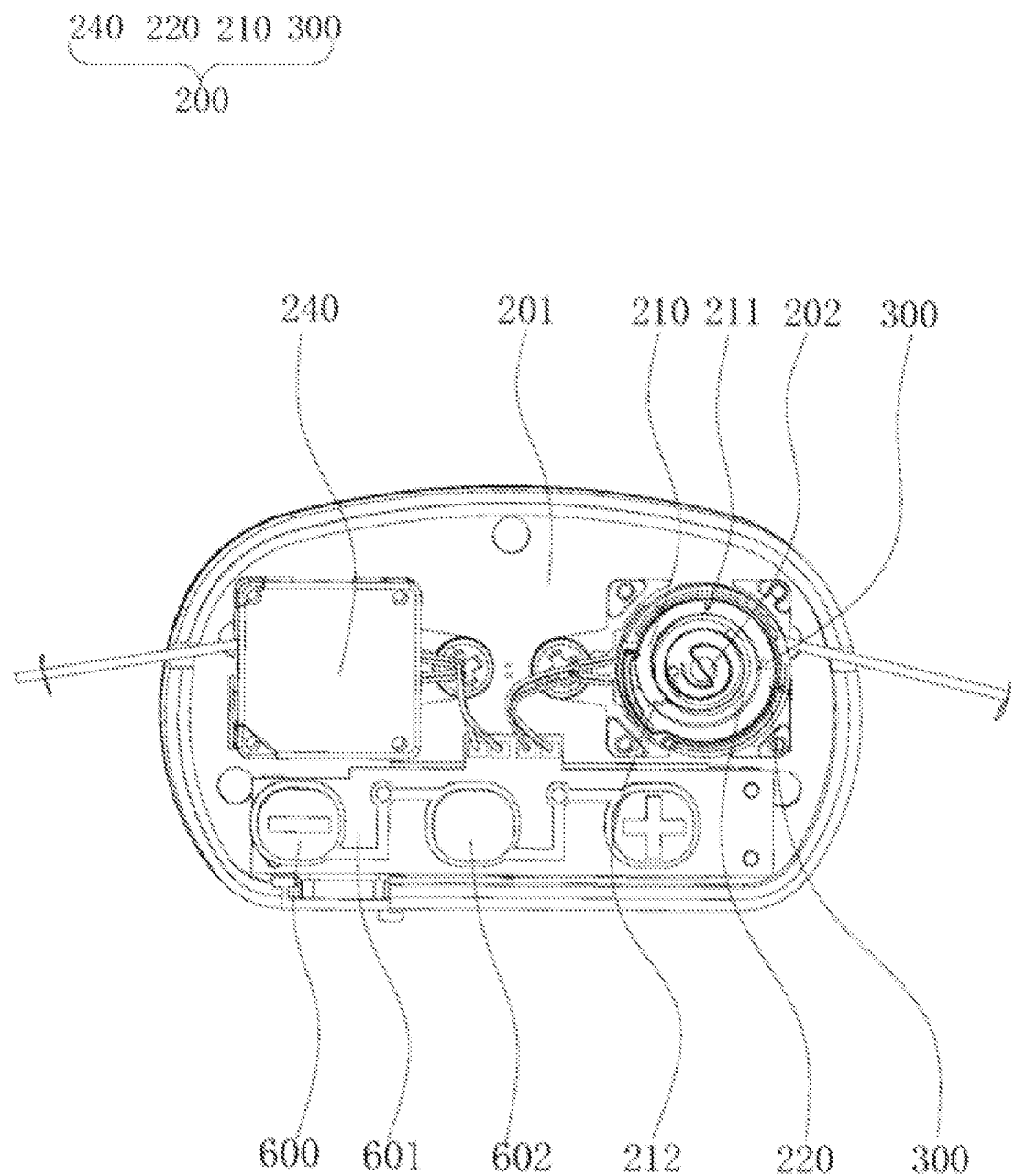
FIG. 2 is a partial view 1 of an eye shield of a sleep noise-proof structure according to an embodiment of the present invention.
Figure 3:
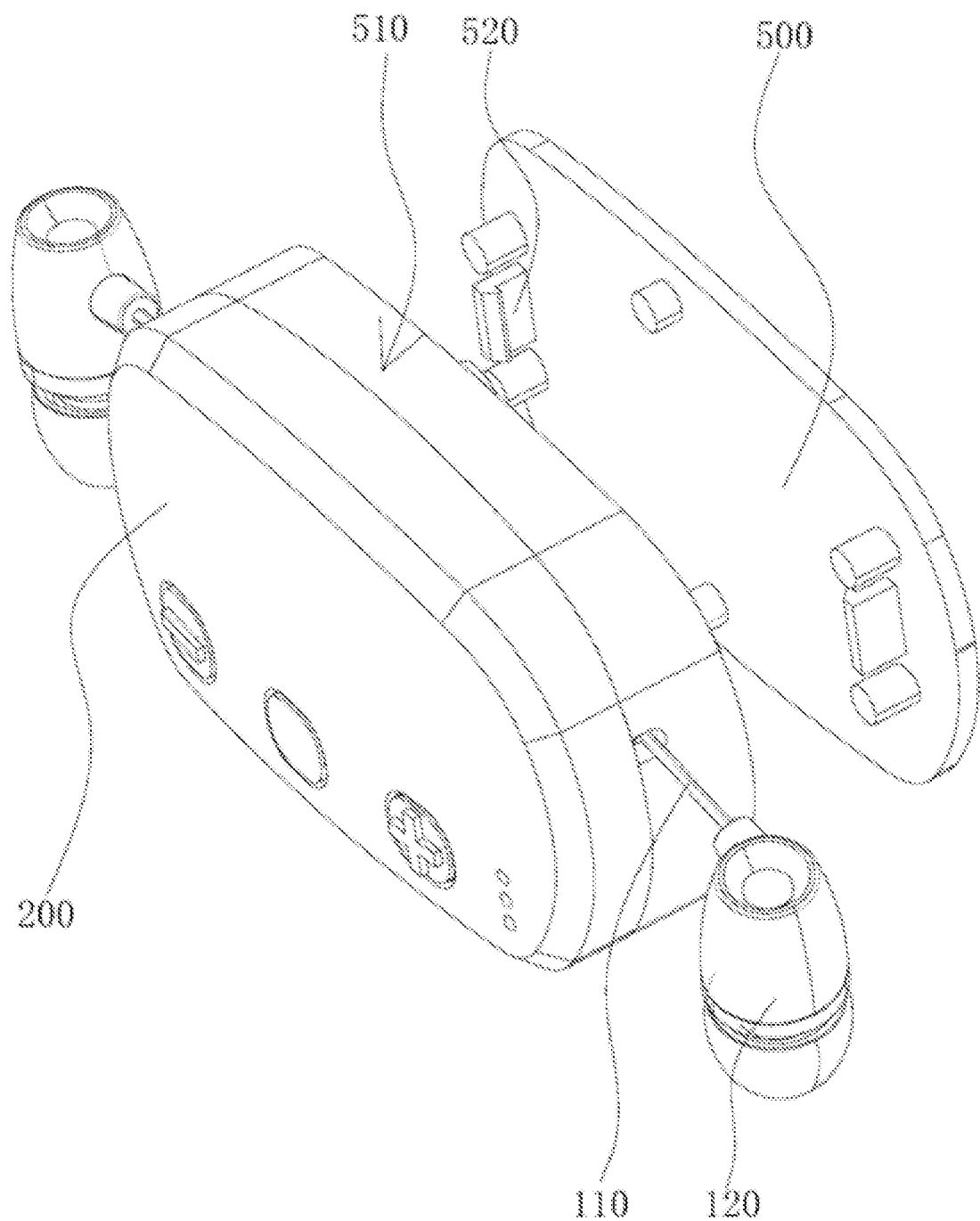
FIG. 3 is a partial view 2 of an eye shield of a sleep noise-proof structure according to an embodiment of the present invention.
Figure 4:
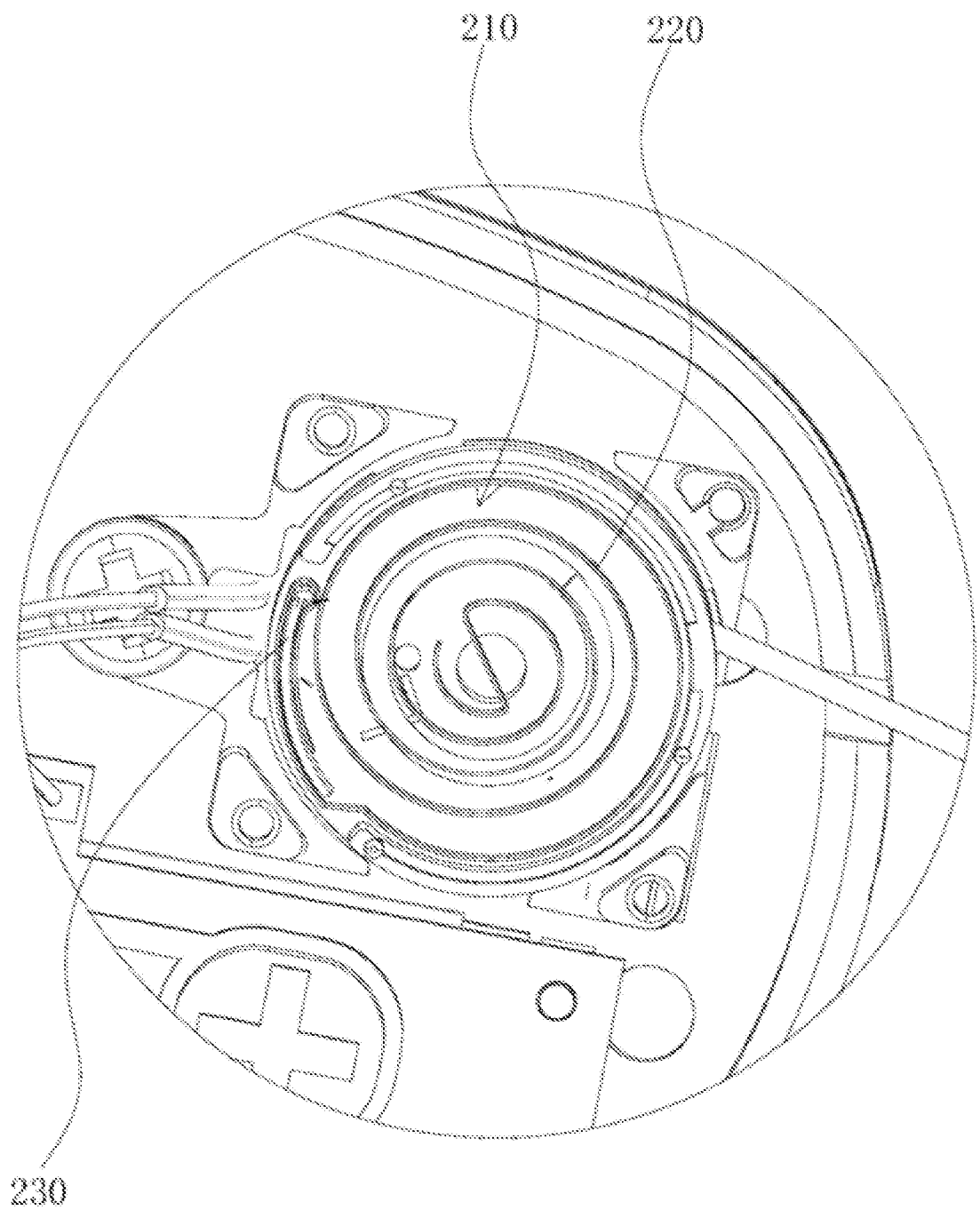
FIG. 4 is a partial view 1 of a mounting housing of a sleep noise-proof structure according to an embodiment of the present invention.
Figure 5:
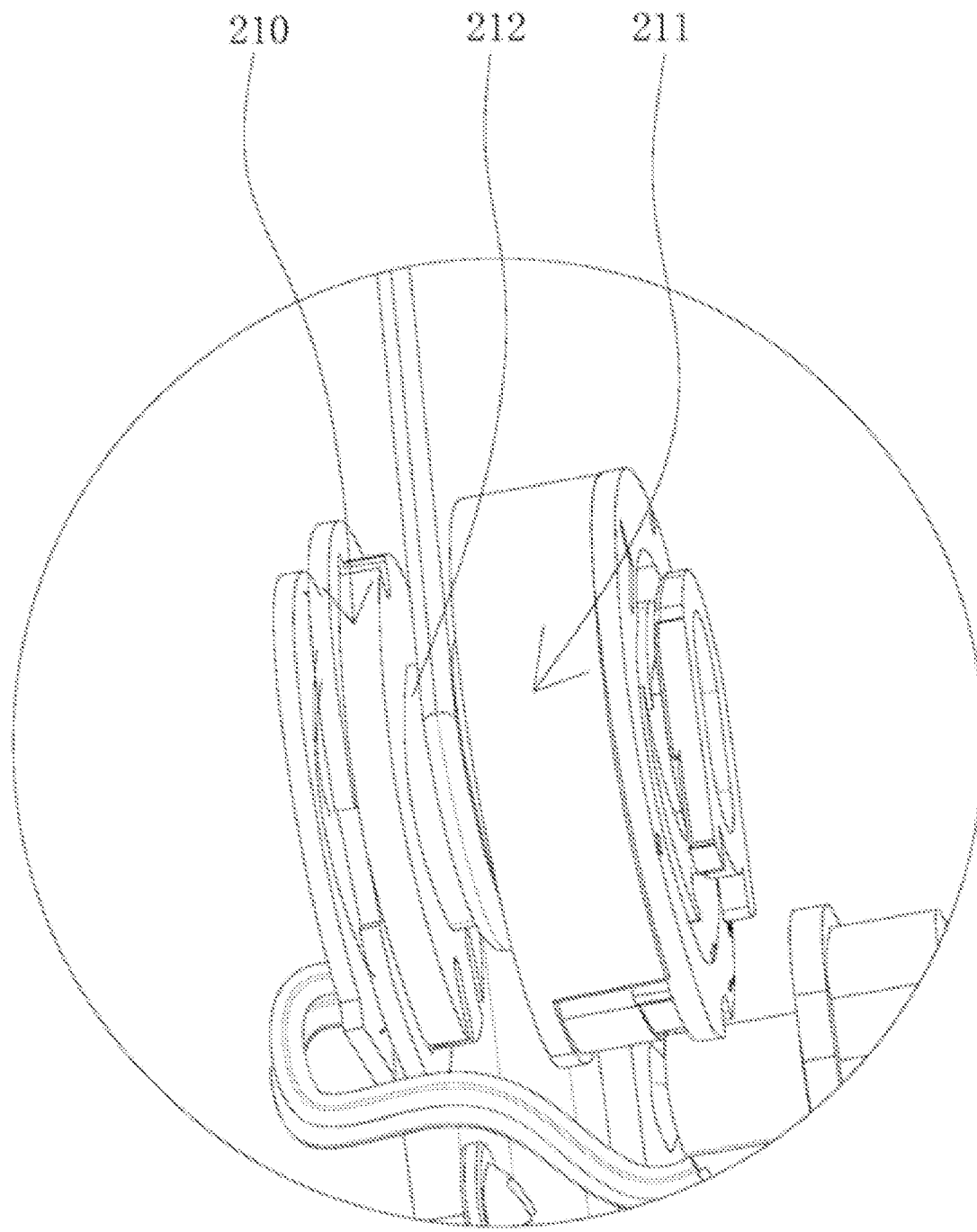
FIG. 5 is a partial view 2 of a mounting housing of a sleep noise-proof structure according to an embodiment of the present invention.
Figure 6:
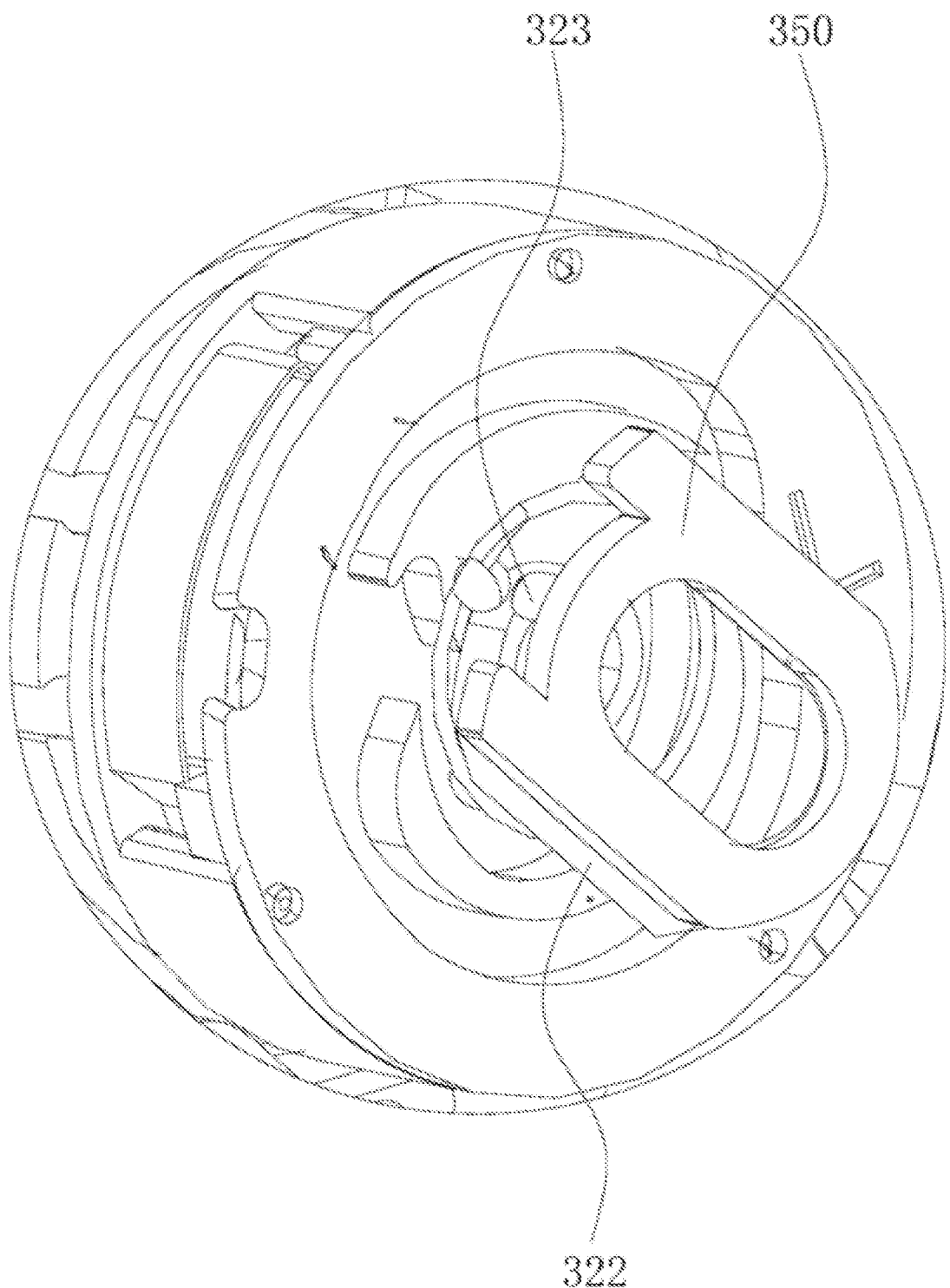
FIG. 6 is a partial view 1 of a positioning assembly of a sleep noise-proof structure according to an embodiment of the present invention.
Figure 7:
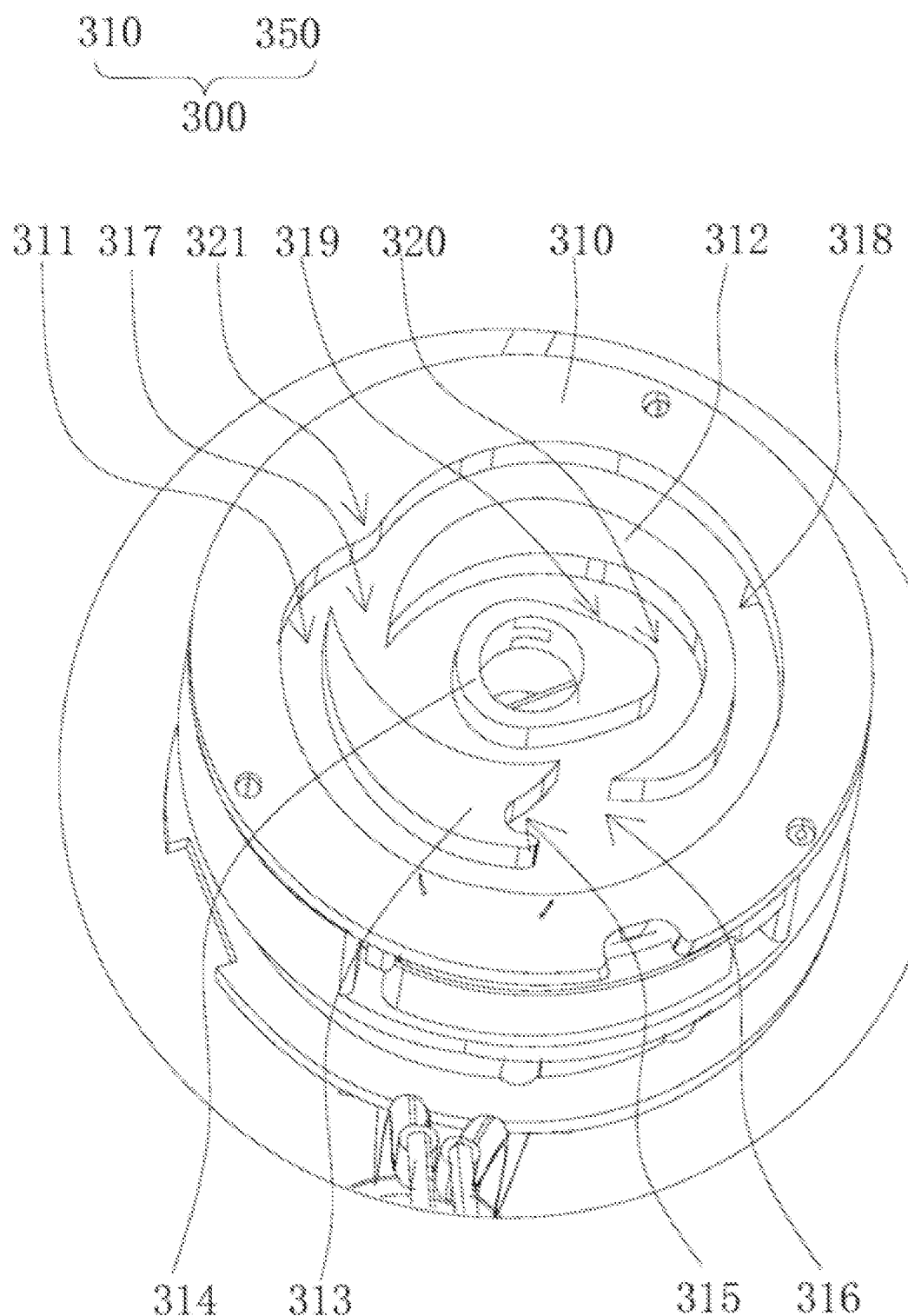
FIG. 7 is a partial view 2 of a positioning member of a sleep noise-proof structure according to an embodiment of the present invention.
Figure 8:
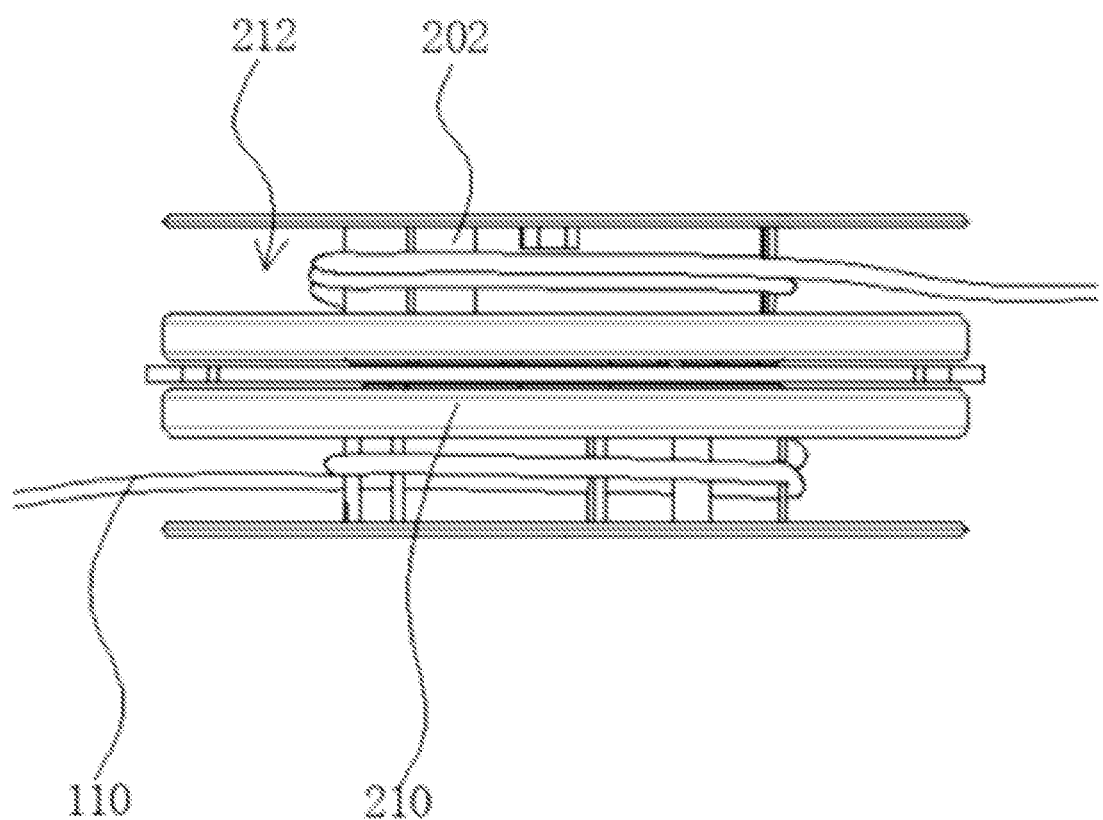
FIG. 8 is a partial view 3 of a positioning member of a sleep noise-proof structure according to an embodiment of the present invention.

Reference will now be made in detail to embodiments of the present invention, examples of which are illustrated in FIGS. 1-8, wherein like reference numerals refer to the same or similar elements or elements having the same or similar functions throughout. The embodiments described below with reference to FIGS. 1 to 8 are exemplary and are intended to explain embodiments of the present invention and are not to be construed as limiting the present invention.

In the description of the embodiments of the present invention, it is to be understood that the terms "length", "width", "upper", "lower", "front", "rear", "left", "right", "vertical", "horizontal", "top", "bottom", "inner", "outer", etc. designate orientations or positional relationships based on the orientations or positional relationships shown in the drawings, merely to facilitate the description of the embodiments of the present invention and simplify the description, and do not indicate or imply that the intended apparatuses or elements must have a particular orientation, be constructed and operated in a particular orientation, and thus should not be construed as limiting the present invention.

Further, the terms "first" and "second" are used for descriptive purposes only and are not to be construed as indicating or implying relative importance or implicitly indicating the number of technical features indicated. Thus, a feature with "first" or "second" being defined may explicitly or implicitly comprise one or more of the feature. In the description of the embodiments of the present invention, "a plurality" means two or more unless specifically limited otherwise.

In the embodiments of the present invention, unless otherwise explicitly specified or limited, the terms "mounted", "connected", "connected to", "fixed" and the like are to be construed broadly, e.g., as being fixed or detachably connected, or integrated; can be mechanically or electrically connected; they may be directly connected or indirectly connected through intervening media, or may be connected through the use of two elements or the interaction of two elements. For a person skilled in the art, the specific meaning of the above-mentioned terms in the embodiments of the present invention can be understood according to specific situations.

In one embodiment of the present invention, the present case provides a sleep noise-proof structure provided on an eye-shrouding member 100 having eye shields 130 for shielding eyes. The eye-shrouding member 100 may be an ordinary eye patch and a sleeping cap on the market. The sleep noise-proof structure comprises two wires 110 and two earplugs 120, wherein the wires 110 have a first end fixedly connected to the front side of the eye shield 130 and a second end connected to the earplug 120.

In the embodiment of the present invention, the user, at rest, wears the eye-shrouding member 100 of the present embodiment. The earplug 120 may be pulled from the front side of the eye shield 130 and the wire 110 may be pulled back from the front side of the eye shield 130 to insert the earplug 120 into the ear. In this way, a person can be prevented from being disturbed by external noise during rest. Since the earplug 120 is connected to the front side of the eye shield 130 with a wire 110, not only the problem of loss of the earplug 120 can be prevented, but also the ear cannot be tightened.

Further, the wire 110 is a stretching wire and the second end of the wire 110 is free to stretch. In the present embodiment, the user can satisfy different user's requirements according to the length of the wire 110 according to his/her own requirements, without causing excessive wire 110 to be wound into a bunch to cause discomfort to the human body.

Further, the sleep noise-proof structure further includes a reel device 200 including a mounting housing 240, a wire spool 210, a winding spring 220, and a positioning member 300. The mounting housing 240 is provided on the front side of the eye shield 130, a mounting cavity 201 is provided in the mounting housing 240, a support shaft 202 is provided in the cavity of the mounting cavity 201, and the wire spool 210 is rotatably sleeved on the support shaft 202. A concave cavity 211 is provided on the bottom side of the wire spool 210, a winding spring 220 is provided in the concave cavity 211, and one end of the winding spring 220 is snap-fit with the support shaft 202, and the other end thereof is snap-fit with the wire spool 210. A first end of the wire 110 is wound around the wire spool 210 and a second end extends out of the mounting cavity 201. A positioning member 300 is provided in the mounting cavity 201 for positioning the wire spool 210. In the present embodiment, it is a function that the second end of the wire 110 can be freely stretched and also automatically retracted. Specifically, when the wire 110 is pulled out, the wire spool 210 rotates, the wire 110 wound on the wire spool 210 is released, and the winding spring 220 is wound. After the wire 110 is pulled out to a desired length, the wire 110 can be pulled out to a desired length according to the user's requirements by positioning the wire spool 210 with the positioning member 300 to prevent the wire spool 210 from rotating. When the wire 110 needs to be recovered, the wire spool 210 is released through the positioning member 300, and the wire spool 210 is rotated in the opposite direction by the winding spring 220, so that the wire 110 is wound on the wire spool 210.

Further, the wire spool 210 is provided with two wire grooves 212, and a wire 110 is connected to each wire groove 212. In the present embodiment, the two wires 110 are wound and released simultaneously by a single wire spool 210.

Further, the reel devices 200 are in two groups, and each of the wires 110 is connected to one of the reel devices 200. In the present embodiment, the reel device 200 may be used to control and adjust the movement between the winding springs 220 and the wires 110. Since each wire 110 is connected to a wire spool 210, the earplugs 120 may be pulled by pulling on the wires 110, while the winding springs 220 may also provide a degree of resilient support.

Further, the positioning member 300 includes a track board 310 and a retaining ring 350. The track board 310 is provided on one side of the wire spool 210, a limiting cavity 311 is provided on an upper end face of the track board 310, and an outer guide 312, a limiting member 313 and an inner guide 314 are provided in the limiting cavity 311. One end of the limiting member 313 is provided with a limiting slot 315, an outlet 316 is formed between one end of the outer guide 312 and one end of the limiting slot 315 of the limiting member 313, and the other end of the outer guide 312 and one end of the limiting member 313 facing away from the limiting slot 315 form an inlet 317. The outer side of the outer guide 312 and the inner side of the limiting cavity 311 form an outer track 318, the inner side of the limiting member 313 and the outer side of the inner guide 314 form an inner track 319, the inner guide 314 has a high point 320 away from the center of the support shaft 202, the high point 320 is arranged close to the outlet 316, the inner side of the limiting cavity 311 is provided with a guide boss 321 extending towards the inlet 317, the guide boss 321, and the inlet 317, the outlet 316 and the high point 320 are successively distributed around the center of the support shaft 202. A guide sliding groove 322 is provided in the mounting housing 240, a retaining ring 350 is slidably provided in the guide sliding groove 322, and the retaining ring 350 is provided with a limiting column 323 extending into the limiting cavity. In the present embodiment, as the wire spool 210 rotates, the limiting column 323 continuously slides within the inner track 319 and the outer track 318, pushing the retaining ring 350 to slide within the guide sliding groove 322. When the limiting column 323 slides on the outer track 318, when sliding to the position of the guide boss 321, the original trajectory of the limiting column 323 is changed, so that the limiting column 323 enters into the inner track 319 from the inlet 317; when the limiting column 323 moves to the high point 320, or exceeds the high point 320, and under the elastic force of the spring, the wire spool 210 is reversed; and the trajectory of the limiting column 323 is changed by the high point 320, so that the limiting column 323 is limited in the limiting slot 315, thereby preventing the wire spool 210 from rotating, so as to have a fixed length effect on the pull rope; when it is desired to retract the wire 110 into the wire spool 210, the wire 110 is gently pulled so that the limiting column 323 enters the outer track 318 along the outlet 316.

Further, the sleep noise-proof structure further comprises a clip board 500, a clip groove 510 is provided on the back side of the mounting housing 240, the clip board 500 is provided with a snap 520, and the snap 520 passes through the eye shield 130 and is engaged with the clip groove 510. In the present embodiment, the snap 520 of the clip board 500 and the clip groove 510 are fastened to each other is not only stable, but also convenient for loading and unloading.

Further, the sleep noise-proof structure further comprises a casing 601, a Bluetooth earphone control module 600 and a battery 602, wherein the casing 601 is arranged on the front side of the eye shield 130. The Bluetooth earphone control module 600, the battery 602 and the reel device 200 are all provided in the casing 601. The wire 110 is an earphone wire and is electrically connected to a control module of the Bluetooth earphone, and a loudspeaker module is provided in the earplug 120.

In the present embodiment, since the Bluetooth earphone control module 600 uses a wireless connection, it does not need to be connected to a mobile phone or the like through the wire 110, and is more convenient to use. Because of the presence of the Bluetooth earphone control module 600, it can be used to control functions such as playing music, answering calls, etc. The earplug 120 is provided with a loudspeaker module therein, and the wire 110 is connected to the Bluetooth earphone control module 600, so that the earplug can receive sound clearly and ease the mood during use.

The above is merely a preferred embodiment of the present invention and is not intended to limit the present invention. Any modifications, equivalents, and improvements made within the spirit and principles of the present invention are intended to be included within the scope of the present invention.

The invention claimed is:
1. A sleep noise-proof structure, provided on an eye-shrouding member being an eye patch or a sleeping cap and having an eye shield for shielding an eye, the sleep noise-proof structure comprising two wires and two earplugs, the wires each having a first end and a second end, each first end being fixedly connected to a front side of the eye shield that faces away from a wearer when worn, each second end being connected to the respective earplugs, wherein the wires are stretching wires, the second end of each wire is freely stretchable, the sleep noise-proof structure further comprises a reel device comprising a mounting housing, a wire spool, a winding spring and a positioning piece; the mounting housing is directly and centrally arranged on the front side of the eye shield, a mounting cavity is arranged in the mounting housing, a support shaft is arranged in the mounting cavity, and the wire spool is rotatably sleeved on the support shaft; a concave cavity is provided on a bottom side of the wire spool, the winding spring is provided to be wound in the concave cavity, and one end of the winding spring is snap-fit with the support shaft, and another end thereof is snap-fit with the wire spool; the first end of one of the wires is wound around the wire spool and the second end of the one of the wires extends out of the mounting cavity; and the positioning piece is provided within the mounting cavity for positioning the wire spool.

2. The sleep noise-proof structure according to claim 1, wherein the number of reel devices is two and each of the wires is connected to a respective one of the reel devices.

3. The sleep noise-proof structure according to claim 2, wherein the positioning piece comprises a track board, a retaining ring; the track board is provided on one side of the wire spool, a limiting cavity is provided on an upper end face of the track board, and an outer guide, a limiting member and an inner guide are provided in the limiting cavity; one end of the limiting member is provided with a limiting slot, an outlet is formed between one end of the outer guide and one end of the limiting slot of the limiting member, and another end of the outer guide and another end of the limiting member facing away from the limiting slot form an inlet; an outer side of the outer guide and an inner side of the limiting cavity form an outer track, an inner side of the limiting member and an outer side of the inner guide form an inner track, the inner guide has a high point away from a center of the support shaft, the high point is arranged close to the outlet, the inner side of the limiting cavity is provided with a guide boss extending towards the inlet, and the guide boss, the inlet, the outlet and the high point are successively distributed around the center of the support shaft; a guide sliding groove is provided in the mounting housing, the retaining ring is slidably provided in the guide sliding groove, and the retaining ring is provided with a limiting column extending into the limiting cavity.

4. The sleep noise-proof structure according to claim 1, wherein the sleep noise-proof structure further comprises a casing, a Bluetooth earphone control module and a battery, the casing is provided on the front side of the eye shield; the Bluetooth earphone control module, the battery and the reel device are all arranged in the casing; each wire is an earphone wire and is electrically connected to the control module of the Bluetooth earphone, and a loudspeaker module is provided in each earplug.

5. The sleep noise-proof structure according to claim 4, further comprising a clip board, wherein a back side of the casing is provided with a clip groove, the clip board is provided with a snap engaged with the clip groove through the eye shield.

6. The sleep noise-proof structure according to claim 1, wherein two wire grooves are provided on the wire spool, and each wire is connected to a respective one of the wire grooves.

\* \* \* \* \*